(12) United States Patent
Beeckler et al.

(10) Patent No.: US 10,682,496 B2
(45) Date of Patent: Jun. 16, 2020

(54) CATHETER HANDLE

(71) Applicant: Biosense Webster (Israel) Ltd., Yokneam (IL)

(72) Inventors: Christopher T. Beeckler, Brea, CA (US); Joseph T Keyes, Sierra Madre, CA (US); Kevin J. Herrera, West Covina, CA (US); Athanassios Papaioannou, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 156 days.

(21) Appl. No.: 15/815,394

(22) Filed: Nov. 16, 2017

(65) Prior Publication Data

US 2019/0143079 A1 May 16, 2019

(51) Int. Cl.
| | | |
|---|---|---|
| *A61M 25/01* | (2006.01) |
| *A61N 1/32* | (2006.01) |
| *A61B 18/00* | (2006.01) |
| *A61B 17/00* | (2006.01) |
| *A61M 25/06* | (2006.01) |
| *A61M 25/10* | (2013.01) |

(52) U.S. Cl.
CPC .... *A61M 25/0136* (2013.01); *A61M 25/0108* (2013.01); *A61M 25/0133* (2013.01); *A61B 2017/00318* (2013.01); *A61B 2018/00172* (2013.01); *A61B 2018/00577* (2013.01); *A61M 2025/0166* (2013.01); *A61M 2025/0681* (2013.01); *A61M 2025/1081* (2013.01); *A61N 1/32* (2013.01)

(58) Field of Classification Search
CPC .......... A61M 25/0136; A61M 25/0108; A61M 25/0133; A61M 2205/0166; A61M 25/0105; A61M 2025/0166; A61M 2205/0227; A61B 2017/00318; A61B 18/1492
USPC ....................................................... 604/528
See application file for complete search history.

(56) References Cited

U.S. PATENT DOCUMENTS

| | | | |
|---|---|---|---|
| 5,391,199 A | | 2/1995 | Ben-Haim |
| 5,545,200 A | * | 8/1996 | West ................. A61B 18/1492 606/29 |
| 6,221,070 B1 | | 4/2001 | Tu et al. |
| 6,239,724 B1 | | 5/2001 | Doron et al. |
| 6,332,089 B1 | | 12/2001 | Acker et al. |
| 6,484,118 B1 | | 11/2002 | Govari |
| 6,618,612 B1 | | 9/2003 | Acker et al. |
| 6,690,963 B2 | | 2/2004 | Ben-Haim et al. |

(Continued)

FOREIGN PATENT DOCUMENTS

WO   WO 96/05768 A1   2/1996

OTHER PUBLICATIONS

International Search Report dated Feb. 14, 2019, International Application No. PCT/IB2018/058782.

*Primary Examiner* — Bhisma Mehta
*Assistant Examiner* — Nidah M Hussain

(57) ABSTRACT

A medical instrument includes first and second knobs. The first knob is fitted on a handle of the medical instrument, and is movable along a longitudinal axis of the medical instrument to control a deflection of a medical device coupled to a distal end of the medical instrument relative to the longitudinal axis. The second knob is fitted on the handle of the medical instrument, and is movable along the longitudinal axis to control a shape of the medical device.

10 Claims, 3 Drawing Sheets

(56) References Cited

U.S. PATENT DOCUMENTS

| | | |
|---|---|---|
| 6,913,600 B2 | 7/2005 | Valley et al. |
| 9,579,448 B2 | 2/2017 | Chow et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2009/0299282 A1 | 12/2009 | Lau et al. |
| 2011/0112524 A1 | 5/2011 | Stern et al. |
| 2014/0276811 A1 | 9/2014 | Koblish et al. |
| 2017/0056087 A1 | 3/2017 | Buckley et al. |
| 2017/0196690 A1 | 7/2017 | Racchini et al. |
| 2019/0069949 A1* | 3/2019 | Vrba ............... A61B 18/1492 |

\* cited by examiner

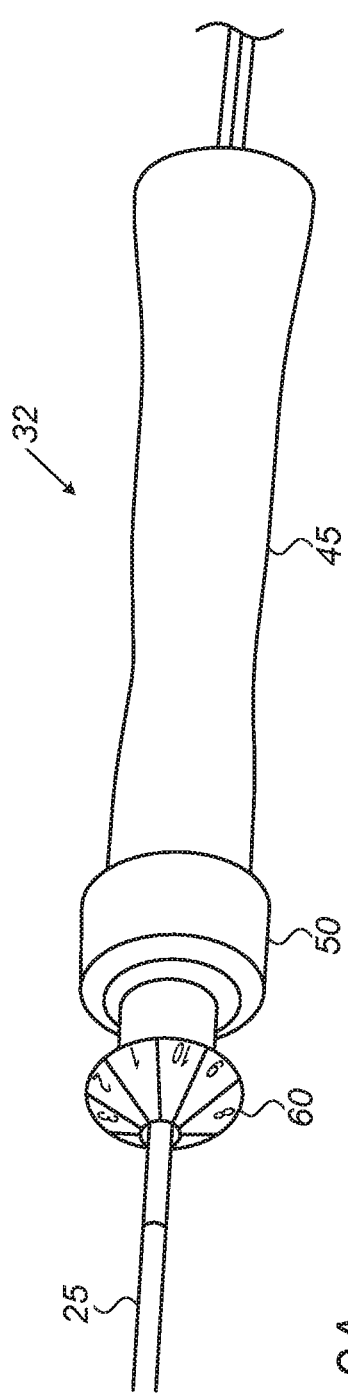
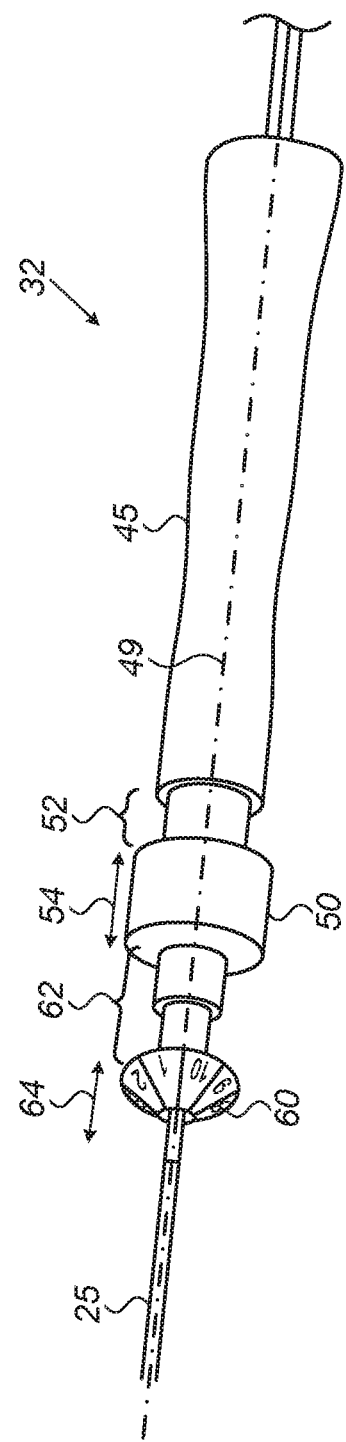
FIG. 2A
FIG. 2B

CATHETER HANDLE

FIELD OF THE INVENTION

The present invention relates generally to catheters, and particularly to methods and systems for controlling deflection and shape of balloon catheters.

BACKGROUND OF THE INVENTION

Balloon catheters may be used in various medical procedures, such as in cardiac ablation. The balloon catheter is typically controlled remotely by a physician. Method and devices for controlling the operation of balloon catheters are known in the art.

For example, U.S. Pat. No. 9,579,448 describes a medical device for the treatment and irrigation of a sinus opening is described. The device allows for single-handed operation to access, dilate and irrigate a sinus opening. The device includes a sinus guide catheter, a guiding element, a balloon dilation catheter, a balloon catheter movement mechanism and a guiding element movement mechanism.

U.S. Pat. No. 6,221,070 describes a steerable ablation catheter system suitable for radiofrequency ablation of intracardiac tissue that comprises two parts: a disposable catheter shaft with a deflectable tip at the distal end of the shaft, and a handle with steering mechanisms.

SUMMARY OF THE INVENTION

An embodiment of the present invention that is described herein provides a medical instrument including first and second knobs. The first knob is fitted on a handle of the medical instrument, and is movable along a longitudinal axis of the medical instrument to control a deflection of a medical device coupled to a distal end of the medical instrument relative to the longitudinal axis. The second knob is fitted on the handle of the medical instrument, and is movable along the longitudinal axis to control a shape of the medical device.

In some embodiments, the first knob is configured to apply first and second levels of deflection of the medical device relative to the longitudinal axis of the medical instrument by being set at respective selected first and second positions along the longitudinal axis of the medical instrument. In other embodiments, the second knob is configured to set the medical device to first and second shapes by being set at respective selected first and second positions along the longitudinal axis of the medical instrument. In yet other embodiments, the first and second knobs are configured to operate independently of one another.

In an embodiment, at least one of the first and second knobs is movable, within a continuous range, along the longitudinal axis. In another embodiment, the handle includes a grip located in proximity to the first and second knobs, such that both the first and second knobs are accessible by one or more fingers of an operator hand that holds the grip. In yet another embodiment, the medical device is configured to be applied in a medical procedure selected from a list consisting of electrophysiology, ablation, sinuplasty, surgery, endoscopy, angioplasty, otolaryngology and neurology.

In some embodiments, the medical device includes an inflatable balloon catheter having an internal volume configured to receive inflation fluid. In other embodiments, the second knob is configured, when moved in a first direction along the longitudinal axis, to allow an inflation of the internal volume of the balloon catheter, and when moved in a second direction along the longitudinal axis, to deflate the balloon catheter by elongating the balloon and forcing the inflation fluid out of the internal volume. In yet other embodiments, the inflatable balloon catheter includes one or more electrodes coupled to an outer surface of the inflatable balloon catheter.

In an embodiment, the medical device includes at least one of electrodes and sensors coupled to the medical device at predefined positions, and at least one of the first and second knobs includes one or more markers indicative of the respective positions of the at least one of electrodes and sensors. In another embodiment, each of the one or more markers includes a respective number of an electrode or a sensor of the at least one of electrodes and sensors.

There is additionally provided, in accordance with an embodiment of the present invention, a method including inserting a medical device coupled to a distal end of a medical instrument into a patient organ. A deflection of the medical device, relative to a longitudinal axis of the medical instrument, is controlled by moving a first knob, which is fitted on a handle of the medical instrument, along the longitudinal axis. A shape of the medical device is controlled by moving a second knob, which is fitted on the handle of the medical instrument, along the longitudinal axis of the medical instrument. A medical procedure is conducted in the patient organ using the medical device.

The present invention will be more fully understood from the following detailed description of the embodiments thereof, taken together with the drawings in which:

BRIEF DESCRIPTION OF THE DRAWINGS

FIGS. 2A and 2B are schematic, pictorial illustrations of a balloon catheter control handle, in accordance with an embodiment of the present invention.

DETAILED DESCRIPTION OF EMBODIMENTS

Overview

Figure 1:
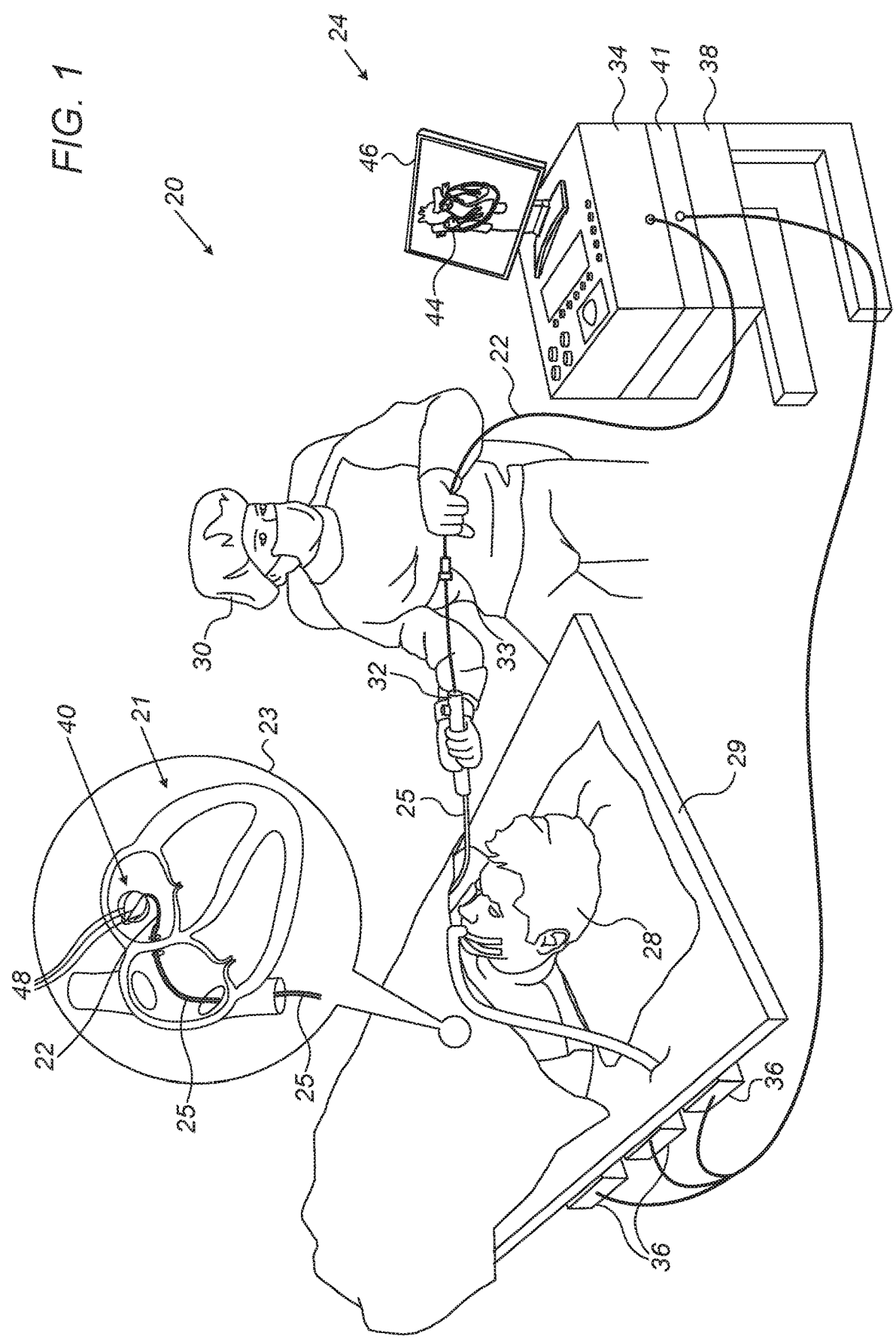
FIG. 1 is a schematic, pictorial illustration of a catheter-based tracking and ablation system, in accordance with an embodiment of the present invention.

Catheters are used, for example, in various interventional cardiology procedures, such as in treating arrhythmia, by ablating the heart tissue so as to form a lesion that blocks electrical conduction along a path of the heart tissue. A catheter used for ablation may comprise an inflatable balloon assembly having an array of devices, such as ablation electrodes, mounted on an outer surface of the balloon assembly. A catheter of this sort is referred to herein as a balloon catheter.

Embodiments of the present invention that are described hereinbelow provide improved techniques for controlling the operations of inflation and deflection of a balloon catheter.

During an ablation procedure, a physician typically starts with a deflated balloon for navigating the catheter to a target location in a patient heart. At the target location, the physician inflates the balloon so as to make physical contact between at least some of the ablation electrodes and heart tissue at the target location. In some cases, the physician may have to deflect the balloon assembly relative to the longitudinal axis of the catheter, so as to better reach the target tissue and/or improve the physical contact with the tissue.

In some embodiments, the catheter comprises a handle, which is coupled to the catheter proximal end, and which is configured to control the balloon assembly at the catheter distal end. At least first and second knobs are fitted on the handle and are movable along the longitudinal axis of the catheter. The first knob is configured to control a deflection of the balloon assembly relative to the longitudinal axis, and the second knob is configured to control the shape of the balloon catheter by elongating the balloon, thus collapsing it and forcing out inflation fluid through existing holes in the balloon. In some embodiments, the first and second knobs are configured to operate independently of one another, such that the physician may inflate or deflate the balloon assembly before or after deflecting the distal end of the catheter, or in any other suitable operational sequence.

In some embodiments, the level of inflation of the balloon assembly and the level of deflection of the distal end are each controllable in a continuous manner. In an exemplary sequence, the physician may deflect the distal end to its maximal deflection level after inflating a portion (e.g., half) of the internal volume of the balloon assembly, and subsequently, the physician inflates the balloon assembly to a fully inflated position.

The disclosed techniques improve the patient safety by providing the physician with easy control of the inflation and deflection operations of the balloon catheter using a single finger. When using the disclosed techniques, the physician can focus his or her attention on the essence of the procedure rather than on the technical manipulation of the balloon catheter.

Furthermore, the disclosed techniques may increase the success rate of ablation procedures by enabling accurate positioning of the ablation electrodes at the target locations of the tissue.

System Description

FIG. 1 is a schematic, pictorial illustration of a catheterization system 20, in accordance with an embodiment of the present Invention. System 20 comprises a medical instrument, such as a balloon catheter 22, and a control console 24. In the embodiment described herein, catheter 22 may be used for any suitable therapeutic and/or diagnostic purposes, such as for ablating tissue or sensing electrophysiological (EP) signals from a heart 21 of a patient 28.

In some embodiments, console 24 comprises a processor 34 having suitable front end and interface circuits for receiving signals from catheter 22, and for controlling other components of system 20.

In some embodiments, processor 34 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In some embodiments, console 24 further comprises a memory 38 and a display 46, which is configured to display data, such as an image 44 of at least part of heart 21. In some embodiments, image 44 may be acquired using any suitable anatomical imaging system.

Reference is now made to an inset 23. A physician 30 inserts a shaft 25 through the vascular system of patient 28 lying on a table 29. In some embodiments, catheter 22 comprises a balloon assembly 40 fitted at the distal end of shaft 25. During the insertion of shaft 25, balloon assembly 40 is maintained in a collapsed position by a sheath (not shown). By containing assembly 40 in the collapsed position, the sheath also serves to minimize vascular trauma along the way to a target location.

In some embodiments, physician 30 navigates balloon assembly 40 to the target location, such as a left atrium or another cavity of heart 21, by manipulating shaft 25 using control handles 32 and 33 coupled to the proximal end of catheter 22.

In some embodiments, physician applies handle 32 for controlling the navigation of shaft 25 and for manipulating the distal end of catheter 22, e.g., so as to make contact between assembly 40 and tissue of heart 21, as will be described in detail in FIG. 2B below. Once the distal end of shaft 25 has reached the target location, physician 30 extracts assembly 40 out of the sheath, referred to herein as an "unextended position," and allows a pump, such as an irrigation pump (not shown), to inflate balloon assembly 40 to an expanded position, as will also be described in detail in FIG. 2B below.

In some embodiments, the proximal end of catheter 22 is connected to interface circuitry in processor 34, and is described in further detail in FIGS. 2A and 2B below.

In some embodiments, the position of distal-end assembly 40 in the heart cavity is typically measured using position sensing techniques. This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, console 24 comprises a driver circuit 41, which drives magnetic field generators 36 placed at known positions external to patient 28, e.g., below the patient torso.

In some embodiments, when the distal end of catheter 22 is positioned in the target location (e.g., the cavity of heart 21), physician 30 extracts balloon assembly 40 out of the sheath and applies handle 32 to manipulate assembly such that an outer surface of assembly 40 makes a physical contact with tissue of the cavity.

In some embodiments, balloon assembly 40 comprises an inflatable balloon (not shown) made from polyethylene terephthalate (PET), polyurethane, polyamide, or any other suitable flexible material. The inflatable balloon is configured to receive inflation fluid into an internal volume of balloon assembly 40.

In some embodiments, physician 30 may apply handle 32 to bring balloon assembly 40 to a non-extended position and allow it to fill with the inflation fluid, or by using any other suitable inflation technique. The level of inflation determines the shape of assembly 40 so that, in some embodiments, handle 32 is configured to control the level of inflation as will be described in detail in FIG. 2B, as well as in the method described in FIG. 3 below.

In some embodiments, handle 32 is further configured to control a deflection level of balloon assembly 40 relative to a longitudinal axis of catheter 22. In case the contact between assembly 40 and the heart tissue is insufficiently firm, physician 30 may apply handle 32 to deflect assembly 40 so as to make improved contact between assembly 40 and the heart tissue.

In some embodiments, physician 30 may determine the levels of inflation and deflection of assembly 40 by setting one or more knobs (typically two knobs as shown in FIGS. 2A and 2B) of handle 32 to a selected position.

In some embodiments, the operations of inflation and deflection may be carried out separately (e.g., an inflation operation followed by a deflection operation), in parallel (e.g., setting both the shape of the balloon and the deflection level simultaneously), alternately (e.g., by setting an initial shape followed by initial deflection, and subsequently inflating (or deflating) assembly 40 to a final shape and deflecting again so as to better reach the target tissue and achieve the intended level of physical contact between assembly 40 and the heart tissue. In other embodiments, any other suitable sequence of operations, or a different combination of the operations described above, may be used.

In some embodiments, assembly 40 further comprises one or more electrodes 48 (ten electrodes in the example of FIG. 1), coupled to the outer surface of assembly 40 and configured to exchange electrical signals with the proximal end of catheter 22 and to conduct the electrical signals to or from the tissue of heart 21. During a medical procedure, such as cardiac EP mapping or tissue ablation, electrodes 48 are brought into contact with the tissue of heart 21, so as to sense electrical signals originated therefrom, or to apply ablation signals for ablating the tissue as described above.

In the context of the present disclosure, the term "electrodes" refers to sensing electrodes or to ablating electrodes configured to sense electrical signals from heart 21 or to ablate tissue of heart 21, respectively.

The configuration of system 20 shown in FIG. 1 is an example configuration, which is chosen purely for the sake of conceptual clarity. In alternative embodiments, any other suitable configuration can also be used. For example, the size and shape of distal-end assembly 40, and additional components, such as thermocouples and irrigation holes may be implemented in any suitable location in assembly 40.

Controlling the Shape and Deflection of the Balloon Assembly

FIG. 2A is a schematic, pictorial illustration of handle 32 in a home position, in accordance with an embodiment of the present invention.

In some embodiments, handle 32 comprises a grip 45, typically located at the proximal end of handle 32 and held by a hand of physician 30. In the example of FIG. 1 physician 30 holds handle 32 in one hand, and uses the other hand located near the end of the sheath to further control the movement. We generally assume that the physician holds the catheter by his or her right hand, but a left-handed person may hold the handle by the left hand.

In some embodiments, handle 32 comprises a deflection knob 50, which is configured to move along a longitudinal axis (shown in FIG. 2B) of catheter 22 so as to control the deflection of assembly 40 relative to the longitudinal axis of catheter 22. In some embodiments, physician 30 may use the thumb (or one or more other fingers) of his or her right hand (i.e., the same hand holding the catheter handle) to advance knob 50, so as to deflect assembly 40 relative to the longitudinal axis of catheter 22.

In similar embodiments, physician 30 may use one or more fingers of his or her right hand to retract knob 50, so as to align assembly 40 relative to the longitudinal axis of catheter 22.

In some embodiments, handle 32 comprises a shape-control knob 60, which is configured to control the shape of balloon assembly 40. As described in FIG. 1 above, physician 30 may apply control knob 60 to control the shape of assembly 40 by elongating the balloon of assembly 40, thus collapsing it and forcing out the inflation fluid through existing holes in the balloon.

In some embodiments, physician 30 may control the shape of assembly 40 by moving shape-control knob 60 using one or more fingers in a similar manner as described above for deflection knob 50.

Note that both deflection knob 50 and shape-control knob 60 are located in close proximity to grip 45, such that when physician holds grip 45, for example, using his or her right hand, each of deflection knob 50 and control knob 60 is accessible by one or more fingers (e.g., the thumb) of the same hand that holds grip 45.

In the example of FIG. 2A, deflection knob 50 and shape-control knob 60 are fully retracted so that assembly 40 is not inflated and is substantially aligned with the longitudinal axis of catheter 22. This position is referred to herein as a "home position," which is the typical position of assembly 40 during introduction through the sheath.

FIG. 2B is a schematic, pictorial illustration of handle 32 in an extended position, in accordance with an embodiment of the present invention. In the context of the present disclosure and in the claims, the terms "expanded position", "extended position" and "inflated position" are used interchangeably and refer to a position in which balloon assembly 40 is fully (or partially) inflated with the inflation fluid.

In some embodiments, physician 30 may move deflection knob 50 over a deflection setting range 52 along axis 49 of handle 32, in directions represented by a two-way arrow 54, so as to set the degree of deflection of assembly 40 relative to axis 49. For example, physician 30 may move deflection knob 50 to one end of deflection setting range (e.g., the distal end), so as to obtain the maximal level of deflection of assembly 40, and may similarly align assembly 40 with axis 49 by setting deflection knob 50 at the opposite (e.g., proximal) end of deflection setting range 52. In some embodiments, the handle comprises mechanical stoppers at the ends of deflection setting range 52.

In the example of FIG. 2A, deflection knob 50 is fully retracted to the proximal end of deflection setting range 52, so that it makes contact with the mechanical stopper, such as the distal end of grip 45 that is configured to limit the motion of knob 50 within deflection setting range 52.

In the example of FIG. 2B, knob 50 is fully advanced to the distal end of deflection setting range 52, so that it makes contact with the mechanical stopper that prevents further deflection of assembly 40.

In some embodiments, shape-control knob 60 is limited to move within a predefined range, referred to herein as a shape setting range 62 having, for example, a similar configuration and operational mode described above for the deflection setting range of deflection knob 50.

In some embodiments, physician may advance shape-control knob 60 along shape setting range 62, so as to extract the distal end of the balloon of assembly 40 to the unextended position, and to allow the irrigation pump to inflate the balloon with inflation fluid (not shown). In these embodiments, by sliding shape-control knob 60 forward to a certain position, physician 30 sets the shape of balloon assembly 40.

In an embodiment, physician 30 may advance shape-control knob 60 along axis 49 in directions represented by a two-way arrow 64, to the distal end of shape setting range 62 so as to set assembly 40 in an "inflated position."

Similarly, physician 30 may retract shape-control knob 60 to the proximal end of shape setting range 62, referred to herein as "home position" of knob 60 as shown in FIG. 2A. In the home position of knob 60, the balloon of assembly 40 is elongated so that the inflation fluid is forced out of the internal volume of assembly 40, e.g., into the body of patient 28, or into a reservoir (not shown) of system 20.

Note that, when deflection knob 50 and shape-control knob 60 are, each, positioned at the distal end of respective ranges 52 and 62, assembly 40 is fully deflected relative to axis 49 and is fully inflated. This extended position typically assists physician 30 in manipulating assembly 40 to make the intended contact of the balloon catheter with the target tissue of heart 21.

In some embodiments, deflection knob 50 can be positioned at any point along deflection setting range 52. In alternative embodiments, deflection knob 50 can be set only at one or more predefined positions along the range.

In some embodiments, deflection knob 50 and shape-control knob 60 may be fitted on the distal end of grip 45 as shown in FIG. 2A, or may be coupled to handle 32 using any other suitable configuration and coupling technique. For example, deflection knob 50 and shape-control knob 60 may be fitted on handle 32 side-by-side instead of after one another along axis 49.

In some embodiments, shape-control at least one of knobs 50 and 60 may have one or more numbers marked on the surface, as shown in FIGS. 2A and 2B. In an embodiment, each number indicates a position of a respective electrode 48 on the outer surface of assembly 40, so as to assist physician 30 in knowing the orientation of balloon assembly 40 in heart 21, without relying on a mapping system or X-ray visualization. In other embodiments, the numbers, or any other suitable marker, may be used to indicate the position of any device, such as one or more electrodes and/or sensors coupled to the outer surface of assembly 40.

In the example of FIGS. 2A and 2B, deflection knob 50 and shape-control knob 60 are movable along respective linear ranges (e.g., deflection setting range 52 and shape setting range 62) along axis 49. In alternative embodiments, at least one of these ranges may have a non-linear shape, such as a curved shape or any other suitable shape. For example, deflection knob 50 may control the deflection of assembly 40 by rotating, rather than by moving in a linear range.

Figure 3:
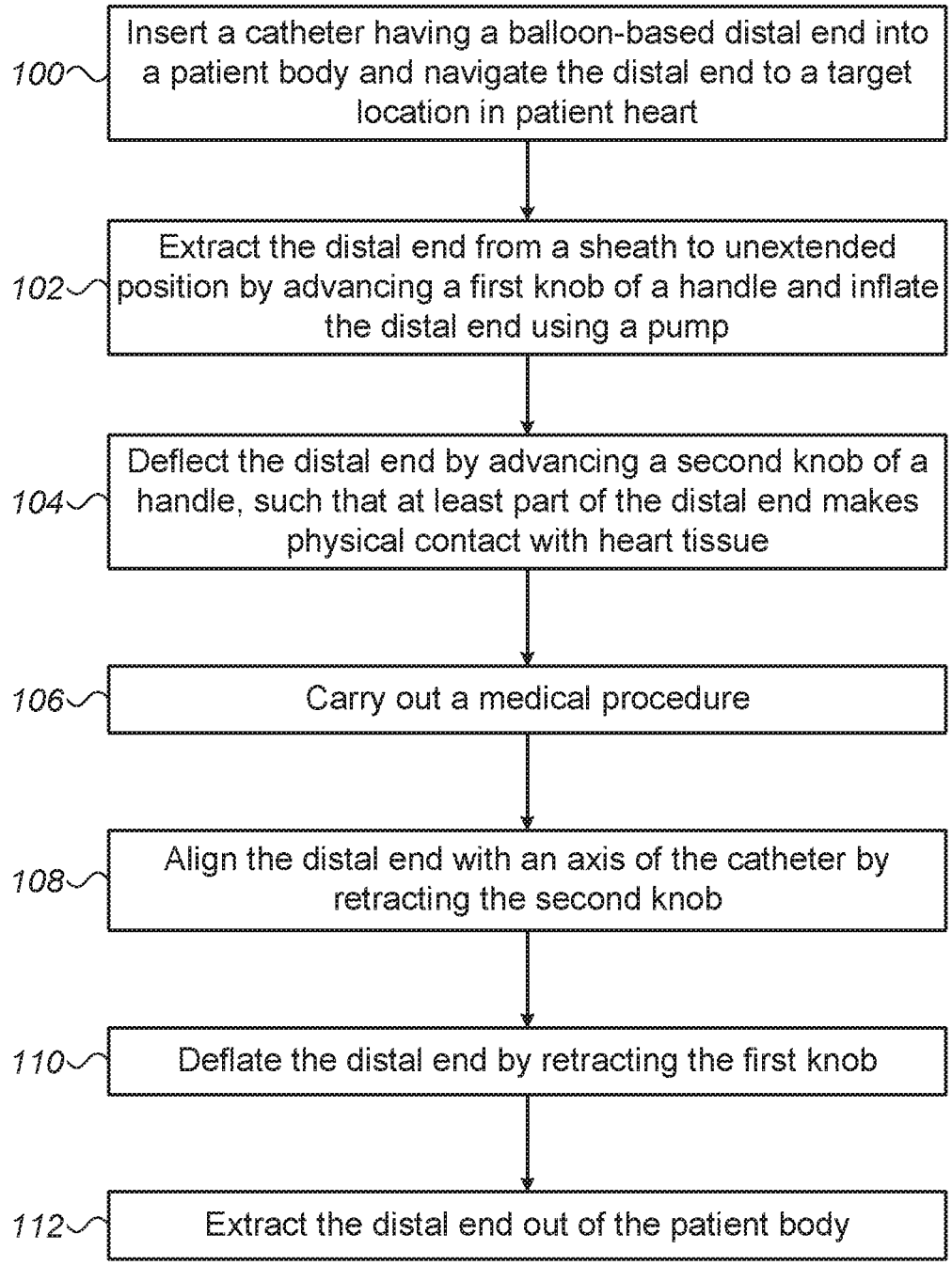
FIG. 3 is a flow chart that schematically illustrates a method for conducting a medical procedure using a balloon catheter, in accordance with an embodiment of the present invention.

FIG. 3 is a flow chart that schematically illustrates a method for conducting a medical procedure using balloon catheter 22, in accordance with an embodiment of the present invention. The method begins at a catheter insertion step 100, with physician 30 inserting catheter 22 into the body of patient 28 and navigating assembly 40 to the cavity of heart 21. At a balloon inflation step 102, physician 30 advances shape-control knob 60 towards the distal end of shape setting range 62, unextending balloon and then inflates assembly 40 with the inflation fluid using the irrigation pump.

At a balloon deflection step 104, physician 30 advances deflection knob 50 towards the distal end of deflection setting range 52, so as to deflect assembly 40 relative to axis 49. In some embodiments, physician 30 may check, after concluding each of steps 102 and 104, whether assembly 40 makes the intended contact with the tissue of heart 21. In case the intended contact is not obtained, physician 30 may repeat step 102 and/or step 104 until the intended contact between assembly 40 and the tissue is obtained.

After bringing assembly 40 into the intended contact with the tissue, physician 30 may carry out the medical procedure, such as ablating the tissue of heart 21, at a treatment step 106. In some embodiments, the medical procedure may involve diagnostics, such as sensing of EP signals from the tissue of heart 21.

After concluding the medical procedure, physician 30 may align assembly 40 with axis 49 by retracting deflection knob 50 to the proximal end of deflection setting range 52, at a distal end alignment step 108.

At a deflating step 110, physician retracts shape-control knob 60 to the proximal end of shape setting range 62, so as to force the fluid out of the internal volume of assembly 40, thereby to set assembly 40 in the unextended position. After concluding step 110, handle 32 is set at home position as shown in FIG. 2A above.

In some embodiments, physician 30 may change the order between steps 102 and 104, or may apply any suitable sequence as described in FIG. 2B above, so as to obtain, before applying the medical procedure at step 106, the intended contact between assembly 40 and the tissue of heart 21.

In some embodiments, after concluding the medical procedure at step 106, physician 30 may change the order between steps 108 and 110, or may apply any other suitable sequence, so as to set handle 32 at home position.

In some embodiments, after inflating balloon assembly 40 at step 100 physician 30 may extract balloon assembly 40 out of the sheath, as described in FIG. 1 above. In some embodiments, after concluding step 110, assembly 40 is in the unextended position and aligned with axis 49. At this stage, physician 30 may insert assembly 40 into the sheath, thereby setting assembly 40 at a collapsed position.

At a retraction step 112, physician retracts catheter 22 so as to extract assembly 40 out of the body of patient 28. Step 112 concludes the method of FIG. 3.

Although the embodiments described herein mainly address cardiac arrhythmia, the methods and systems described herein can also be used in other applications, such as in electrophysiology, ablation of tissue, sinuplasty, surgery, endoscopy, angioplasty, otolaryngology and neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical instrument, comprising:
   a first knob, which is fitted on a handle of the medical instrument, and which is movable along a longitudinal axis of the medical instrument to control a deflection of a medical device coupled to a distal end of the medical instrument relative to the longitudinal axis, wherein the medical device comprises at least one of electrodes and sensors coupled to the medical device at predefined positions; and a second knob, which is fitted on the handle of the medical instrument, and which is movable along the longitudinal axis to control a shape of the medical device, wherein the second knob comprises one or more markers indicative of the respective predefined positions of the at least one of electrodes and sensors.

2. The medical instrument according to claim 1, wherein the first knob is configured to apply first and second levels of deflection of the medical device relative to the longitudinal axis of the medical instrument by being set at respective selected first and second positions along the longitudinal axis of the medical instrument.

3. The medical instrument according to claim 1, wherein the second knob is configured to set the medical device to first and second shapes by being set at respective selected first and second positions along the longitudinal axis of the medical instrument.

4. The medical instrument according to claim 1, wherein the first and second knobs are configured to operate independently of one another.

5. The medical instrument according to claim 1, wherein at least one of the first and second knobs is movable, within a continuous range, along the longitudinal axis.

6. The medical instrument according to claim 1, wherein the handle comprises a grip located in proximity to the first and second knobs, such that both the first and second knobs are accessible by one or more fingers of an operator hand that holds the grip.

7. The medical instrument according to claim 1, wherein the medical device is configured to be applied in a medical procedure selected from a list consisting of electrophysiology, ablation, sinuplasty, surgery, endoscopy, angioplasty, otolaryngology and neurology.

8. The medical instrument according to claim 1, wherein the medical device comprises an inflatable balloon catheter having an internal volume configured to receive inflation fluid.

9. The medical instrument according to claim 8, wherein the inflatable balloon catheter comprises the electrodes coupled to an outer surface of the inflatable balloon catheter.

10. The medical instrument according to claim 1, wherein each of the one or more markers comprises a respective number of an electrode or a sensor of the at least one of electrodes and sensors.

* * * * *